United States Patent [19]

Bhaduri et al.

[11] Patent Number: 4,491,670
[45] Date of Patent: Jan. 1, 1985

[54] CATALYTIC PROCESS FOR THE DIRECT CARBONYLATION OF ORGANIC NITRO COMPOUNDS

[75] Inventors: Sumit Bhaduri; Krishna R. Sharma; Gopalkrishnan S. Kalpathi, all of Thane, India

[73] Assignee: Indian Explosives Ltd., Calcutta, India

[21] Appl. No.: 461,398

[22] Filed: Jan. 27, 1983

[51] Int. Cl.³ ............... C07C 125/06; C07C 118/06
[52] U.S. Cl. ........................ 560/24; 260/453 PC; 560/25; 564/393

[58] Field of Search ............ 260/453 PC; 560/25, 560/24; 564/393

[56] References Cited

U.S. PATENT DOCUMENTS 3,923,850  12/1975  Kober et al. ............ 260/453 PC

Primary Examiner—Dolph H. Torrence
Attorney, Agent, or Firm—Ladas & Parry

[57] ABSTRACT

Isocyanates, or derivatives thereof, are produced from nitrobenzene or 2,4-dinitrotoluene by reaction with carbon monoxide in the presence of an iron, ruthenium, rhodium, or platinum carbonyl as catalyst.

8 Claims, No Drawings

CATALYTIC PROCESS FOR THE DIRECT CARBONYLATION OF ORGANIC NITRO COMPOUNDS

The present invention relates to the preparation of isocyanates or derivatives of isocyanates and more particularly to the preparation of isocyanates or derivatives of isocyanates by direct carbonylation of organic nitro compounds. The reductive carbonylation reaction shown below has two distinct advantages over the usual two step isocyanate syathesis based on phosgene.

$$RNO_2 + 3CO \rightarrow RNCO + 2CO_2$$

First, it avoids the use of highly toxic phosgene and the formation of corrosive hydrochloric acid. Second, the hydrogenation step to convert the nitro compound to the corresponding amine derivative of the conventional process could be avoided, and isocyanate is obtained in a single step.

Although in the prior art there are examples of transition metal complex catalysed direct carbonylation of nitro compounds, the present process, which employs a novel class of metal complexes as catalysts operates at a much reduced pressure with comparable yields and selectivities.

The process involves reaction of an organic compound with carbon monoxide or a mixture of carbon monoxide and any other non-oxidising gas such as nitrogen or argon in a suitable solvent in the presence of a catalyst. By carrying out the reaction in various alcohols the corresponding carbamate derivatives could be obtained. This reaction of alcohols with isocyanates has been known for a long time. Alternatively, pure isocyanate might be synthesised by using very dry solvents that are inert to the isocyanate derivatives.

The organic nitro compound could be nitrobenzene or 2,4 dinitrotoluene. Low conversions and poor selectivities are encountered with 2,4 dinitrotoluene. With nitrobenzene however the conversion as well as the selectivity are much higher.

The pressure and temperature of the reaction influence the overall yield of the isocyanate derivative. Temperatures from 30° C. to 200° C. and pressures from atmospheric to 5000 p.s.i. have been used. The optimum pressure and temperature are about 100 p.s.i. and 140° C.

The reaction could be conveniently carried out in solvents such as tetrahydrofuran, acetonitrile, methanol, ethanol, propanol, isopropanol butanol or aromatic solvents such as benzene or toluene. Alternatively, the nitro compound itself could be used as a solvent. Tetrahydrofuran, alcohols and acetonitrile give better conversions and selectivities than the other solvents. Presence of water in the solvent causes the formation of amine and urea derivatives. Thus from nitro benzene, both aniline and diphenyl urea could be obtained in good yield by carrying out the direct carbonylation in wet tetrahydrofuran.

The catalyst is a polynuclear metal carbonyl or its derivative. They could be designated by the following general formula $M_x(CO)_yL_z^{n-}$, where

| M = | Fe | x = 3 | y = 12 | z = 0 | n = 0 |
|---|---|---|---|---|---|
| | Fe | x = 3 | y = 11 | z = 1 | L = H n = 1 |
| | Ru | x = 3 | y = 12 | z = 0 | n = 0 |
| | Ru | x = 3 | y = 11 | z = 1 | L = H n = 1 |
| | Ru | x = 4 | y = 12 | z = 4 | L = H n = 0 |
| | Rh | x = 6 | y = 16 | z = 0 | n = 0 |
| | Pt | x = 15 | y = 30 | z = 0 | n = 2. |

For polynuclear metal carbonyl anions, i.e. cases where n=0, the counter ion is a tetra-alkyl ammonium group. The catalytic activities of the polynuclear carbonyls vary widely and ruthenium derivatives particularly, $Ru_3(CO)_{12}$, are found to be the most active ones. With iron, platinum and rhodium derivatives fairly rapid de-activation of the catalyst takes place. It is also possible to use a precursor such as ruthenium trichloride trihydrate as the catalyst which under the reaction conditions is converted partially to $Ru_3(CO)_{12}$.

According to the present invention there is provided a process for the preparation of isocyanates or derivatives thereof which comprises reacting nitrobenzene or 2,4 dinitrotoluene with carbon monoxide or a mixture of carbon monoxide and inert as in the presence of a polynuclear metal carbonyl or its derivative as catalyst designated by the formula $M_x(CO)_yL_z^{n-}$, wherein,

| M = | Fe | x = 3 | y = 12 | z = 0 | n = 0 |
|---|---|---|---|---|---|
| | Fe | x = 3 | y = 11 | z = 1 | L = H n = 1 |
| | Ru | x = 3 | y = 12 | z = 0 | n = 0 |
| | Ru | x = 3 | y = 11 | z = 1 | L = H n = 1 |
| | Ru | x = 4 | y = 12 | z = 4 | L = H n = 0 |
| | Rh | x = 6 | y = 16 | z = 0 | n = 0 |
| | Pt | x = 15 | y = 30 | z = 0 | n = 2. |

The following examples should not be considered a limitation but a mere illustration of the invention.

EXAMPLE 1

In an autoclave 100 parts of tetrahydrofuran (not dried) and 100 parts of nitrobenzene were reacted with two parts of triruthenium dodeca carbonyl under an initial pressure of 100 p.s.i. of CO. The mixture was heated at 140° C. for six hours. The product mixture on g.c. analysis showed the formation of 15 parts of phenyl isocyanate, 10 parts of aniline and 25 parts of diphenyl urea.

EXAMPLE 2

In an autoclave 100 parts of prefctly dry acetonitrile and 100 parts of nitrobenzene were reacted with 2 parts of triruthenium codeca carbonyl under an initial pressure of 200 p.s.i. of CO. The mixture was heated at 160° C. for six hours. The product mixture on g.c. analysis showed for formation of 70% of phenyl isocyanate.

EXAMPLE 3

In an autoclave 100 parts of dry ethanol and 100 parts of nitrobenzene were reacted with 2 parts of triruthenium dodecacarbonyl under an initial pressure of 150 p.s.i. of CO. The mixture was treated at 160° C. for six hours. The product mixture on g.c. analysis showed the formation of 65% of $PhNH\ CO_2Et$.

EXAMPLE 4

In an autoclave 100 parts of dry tetrahydrofuran and 100 parts of nitrobenzene were reacted with 2 parts of hexa rhodium hexadeca carbonyl under an initial pressure of 200 p.s.i. of CO. The mixture was heated at 140° C. for six hours. The product mixture on g.c. analysis showed the formation of less than 5% phenyl isocyanate.

EXAMPLE 5

In an autoclave 100 parts of dry ethanol and 100 parts of nitrobenzene were reacted with 2 parts of ruthenium trichloride trihydrate under an initial pressure of 150 p.s.i. of CO. The product mixture on g.c. analysis showed the formation of 10% of Ph NH CO$_2$Et.

EXAMPLE 6

In an autoclave 100 parts of dry tetrahydrofuran and 100 parts of 2,4 dinitroteluene were reacted with 2 parts of triruthenium dodecacarbonyl under an initial pressure of 150 p.s.i. of CO. The mixture was heated at 160° C. for six hours. The product mixture on g.c. analysis showed the formation of 12% of toluene 2,4 di-isocyanate.

We claim:

1. A process for the preparation of isocyanates or derivatives thereof which comprises reacting nitrobenzene or 2,4 dinitrotoluene with carbon monoxide or a mixture of carbon monoxide and inert gas in the presence of a polynuclear metal carbonyl or its derivative as catalyst designated by the formula $M_x(CO)_y L_z^{n-}$, wherein,

| M = Fe | x = 3 | y = 12 | z = 0 | n = 0 | |
|---|---|---|---|---|---|
| Fe | x = 3 | y = 11 | z = 1 | L = H | n = 1 |
| Ru | x = 3 | y = 12 | z = 0 | | n = 0 |
| Ru | x = 3 | y = 11 | z = 1 | L = H | n = 1 |
| Ru | x = 4 | y = 12 | z = 4 | L = H | n = 0 |
| Rh | x = 6 | y = 16 | z = 0 | | n = 0 |
| Pt | x = 15 | y = 30 | z = 0 | | n = 2. |

2. A process as claimed in claim 1 wherein the reaction is conducted at a temperature of from 30° C. to 200° C.

3. A process as claimed in claim 1 wherein the reaction is conducted at a pressure of from 1 atmosphere to 5000 p.s.i.

4. A process as claimed in claim 3 wherein the reaction is conducted in the presence of alcohols such as methanol, ethanol, propanol, isopropanol or butanol as solvents and reactants for the isocyanate products to give the urethane derivatives.

5. A process as claimed in claim 4 wherein the reaction is conducted in the presence of an inert liquid diluent such as tetrahydrofuran, acetonitrile, diglyene, benzene or toluene.

6. A process as claimed in claim 5 wherein ruthenium trichloride trihydrate is the precursor of the triruthenium dodeca carbonyl.

7. A process as claimed in claim 1 wherein the product isocyanate is converted to aniline by water present in the solvent.

8. A process as claimed in claim 1 wherein the inert gas is nitrogen or argon.

* * * * *